United States Patent
Beauchamp et al.

(10) Patent No.: US 10,662,127 B2
(45) Date of Patent: May 26, 2020

(54) OXIDATIVE DEHYDROGENATION OF ETHANE USING CARBON DIOXIDE

(71) Applicant: 8 Rivers Capital, LLC, Durham, NC (US)

(72) Inventors: Damian Beauchamp, Hillsborough, NC (US); Xijia Lu, Durham, NC (US); Mohammad Rafati, Durham, NC (US)

(73) Assignee: 8 Rivers Capital, LLC, Durham, NC (US)

( * ) Notice: Subject to any disclaimer, the term of this patent is extended or adjusted under 35 U.S.C. 154(b) by 0 days.

(21) Appl. No.: 16/113,772

(22) Filed: Aug. 27, 2018

(65) Prior Publication Data

US 2019/0062236 A1 Feb. 28, 2019

Related U.S. Application Data

(60) Provisional application No. 62/550,990, filed on Aug. 28, 2017.

(51) Int. Cl.
| | | |
|---|---|---|
| *C07C 5/333* | (2006.01) | |
| *B01J 8/08* | (2006.01) | |
| *B01J 8/02* | (2006.01) | |
| *C07C 5/42* | (2006.01) | |

(52) U.S. Cl.
CPC .............. *C07C 5/333* (2013.01); *B01J 8/02* (2013.01); *B01J 8/08* (2013.01); *C07C 5/42* (2013.01)

(58) Field of Classification Search
None
See application file for complete search history.

(56) References Cited

U.S. PATENT DOCUMENTS

| 2,604,495 A | 7/1952 | Erkko et al. |
| 3,078,637 A | 2/1963 | Milton |
| 2014/0206920 A1 | 7/2014 | Kang et al. |
| (Continued) | | |

FOREIGN PATENT DOCUMENTS

| CA | 2 561 986 | 4/2008 |
| CN | 1178719 | 4/1998 |
| (Continued) | | |

OTHER PUBLICATIONS

Cheng et al., "Oxidative dehydrogenation of ethane with CO2 over Cr supported on submicron ZSM-5 zeolite", Chinese Journal of Catalysis 36 (2015) 1242-1248. (Year: 2015).*

*Primary Examiner* — Ali Z Fadhel
(74) *Attorney, Agent, or Firm* — Womble Bond Dickinson (US) LLP (57) ABSTRACT

The present disclosure relates to methods and systems suitable for chemical production by dehydrogenation of ethane utilizing carbon dioxide as a soft oxidant. Ethane and carbon dioxide are reacted in a catalytic reactor to produce a reaction product stream comprising at least ethylene and carbon dioxide. The carbon dioxide can be separated for recycling back into the catalytic reactor, and the ethylene can be upgraded using a variety of process units. Heat from the reaction product stream can be recycle for further uses, including reducing the amount of added heating needed in the catalytic reactor. Additional materials, such carbon monoxide, hydrogen, syngas, methanol, methane, ethane, and even heavier hydrocarbons can be provided.

26 Claims, 2 Drawing Sheets

(56) References Cited

U.S. PATENT DOCUMENTS

2017/0137355 A1* 5/2017 Sarsani ................... C01B 3/36
2018/0170836 A1* 6/2018 Pelati .................... C07C 5/3332

FOREIGN PATENT DOCUMENTS

| CN | 1199652 | 11/1998 |
| --- | --- | --- |
| CN | 1339336 | 3/2002 |
| CN | 1084223 | 5/2002 |
| CN | 1085116 | 5/2002 |
| CN | 1515354 | 7/2004 |
| CN | 1161307 | 8/2004 |
| CN | 1216686 | 8/2005 |
| CN | 1718277 | 1/2006 |
| CN | 1318131 | 5/2007 |
| CN | 101733144 | 6/2010 |
| EP | 2 165 997 | 3/2010 |
| WO | WO 2009/155219 | 12/2009 |
| WO | WO 2017/085604 | 5/2017 |

* cited by examiner

OXIDATIVE DEHYDROGENATION OF ETHANE USING CARBON DIOXIDE

CROSS-REFERENCE TO RELATED APPLICATIONS

The present application claims priority to U.S. Provisional Patent Application No. 62/550,990, filed Aug. 28, 2017, the disclosure of which is incorporated herein by reference.

FIELD OF THE DISCLOSURE

The present disclosure provides chemical production processes. In particular, the present disclosure relates to chemical conversion processes utilizing $CO_2$ as an oxidant.

BACKGROUND

Many chemical conversion processes are very energy intensive and can also be the source of various pollutants. For example, known methods for generating ethylene include steam cracking of ethane or naptha, and such processes are known to consume as much as 1% of the world's energy production. The process also results in significant carbon dioxide emissions. In addition, carbon coking (via the Boudouard reaction) of the catalysts used in the cracking processes can result in the deactivation of the catalyst, which can further drive up the cost of the process. Accordingly, there remains a need in the art for further chemical conversion processes.

SUMMARY OF THE DISCLOSURE

The present disclosure relates to chemical production processes utilizing ethane ($C_2H_6$) as a starting material. For example, the present disclosure can provide for the production of ethylene ($C_2H_4$) utilizing ethane as a starting material. The present processes can reduce the energy requirement for the chemical production, can prevent catalyst deactivation, can consume (instead of producing) carbon dioxide ($CO_2$), and can generate other valuable commodity materials, such as hydrogen gas (e.g., via a water gas shift reaction) and/or methanol (e.g., via reverse water gas shift followed by methanol synthesis).

In one or more embodiments, the presently disclosed methods can utilize carbon dioxide as a soft oxidant to perform oxidative dehydrogenation (ODH) of ethane and thus achieve ethylene production through ethane $CO_2$ cracking. The methods can include providing ethane and carbon dioxide into a suitable reactor and utilizing heat supplied from a suitable thermal source (e.g., concentrated solar energy, combustion, geothermal, or industrial sources). One or both of the ethane and the carbon dioxide can be heated prior to passage into the reactor, such as by passage through a heat exchanger, which may utilize waste heat recuperated from a further stage of the conversion method. Oxidative dehydrogenation (ODH) of ethane in the reactor can yield a number of products including ethylene, unconverted ethane, carbon dioxide, carbon monoxide (CO), hydrogen ($H_2$), methane ($CH_4$), water ($H_2O$), and possibly trace amounts of heavier hydrocarbons depending upon the catalyst used and the overall reaction conditions.

Beneficially, the reaction conditions can be optimized to drive the reaction to a desired ratio of reaction products. For example, in some embodiments, ethylene, carbon monoxide, and water can be present as the primary reaction products. In such embodiments, various separation techniques and conversion techniques can be applied to the reaction products to isolate ethylene and to utilize the remaining reaction products in formation of even further materials, such as methanol. In preferred embodiments, the ODH reaction can be carried out so that the reaction products include a larger number of reaction products. As further described herein, the more complex reaction product mixture can then be further processed to isolate desired commodities, recuperate heat, and recycle chemicals for further reaction.

In one or more embodiments, the present disclosure specifically can provide methods for chemical production from ethane. In example embodiments, such methods can comprise: providing ethane and carbon dioxide into a reactor at a molar ratio so that the amount of provided carbon dioxide is in excess of the stoichiometrically required amount for complete reaction with the ethane; reacting the ethane with the carbon dioxide in a reactor in the presence of a catalyst to form a reaction product stream at a temperature of about 450° C. or greater comprising at least ethylene and carbon dioxide; passing the reaction product stream through a primary heat exchanger to withdraw heat therefrom; removing water and optionally any further condensates present in the reaction product stream; compressing the reaction product stream to a pressure of at least 20 bar; separating carbon dioxide from the reaction product stream in a separation unit to provide an upgraded ethylene stream; heating at least a portion of the carbon dioxide separated from the reaction product stream using the heat withdrawn from the reaction product stream to form a stream of heated carbon dioxide; recycling the stream of heated carbon dioxide back into the reactor; and further processing the upgraded ethylene stream to provide at least ethylene as a produced chemical. In further embodiments, the methods can be characterized by one or more of the following statements, which can be combined in any order or number.

The reactor can be a fixed bed reactor catalytic reactor or a fluidized bed catalytic reactor.

The reaction product stream can be at a temperature of about 500° C. to about 800° C.

The reaction product stream can comprise at least 10% by mass carbon dioxide based on the total mass of the reaction product exiting the reactor.

The reaction product stream can comprise about 10% to about 60% by mass carbon dioxide, based on the total mass of the reaction product exiting the reactor.

The primary heat exchanger can be a transfer line exchanger (TLE).

The reaction product stream exiting the primary heat exchanger can be at a temperature of about 200° C. to about 400° C.

Removing water and optionally any further condensates in the reaction product stream can comprise passing the reaction product stream through a condensing unit.

The reaction product stream can be cooled in the condensing unit to about ambient temperature.

Heating at least a portion of the carbon dioxide separated from the reaction product stream using the heat withdrawn from the reaction product stream can comprise passing the carbon dioxide through a secondary heat exchanger against a circulating stream that is heated in the primary heat exchanger using the heat withdrawn from the reaction product stream.

Recycling the stream of heated carbon dioxide back into the reactor can comprise one or more of the following: injecting the stream of heated carbon dioxide directly into the reactor; injecting the stream of heated carbon dioxide into a carbon dioxide source; injecting the stream of heated carbon dioxide into a line delivering carbon dioxide from a carbon dioxide source to the reactor; injecting the stream of heated carbon dioxide into an ethane source; injecting the stream of heated carbon dioxide into a line delivering ethane from an ethane source to the reactor.

The at least a portion of the stream of heated carbon dioxide can be passed through a line heater configured for transfer of heat from the stream of heated carbon dioxide to one or more streams being passed into the reactor.

A portion of the heat withdrawn from the reaction product stream in the primary heat exchanger can be used for heating one or more of the following: the reactor; a carbon dioxide source; a carbon dioxide line delivering carbon dioxide from a carbon dioxide source to the reactor; an ethane source; an ethane line delivering ethane from an ethane source to the reactor.

A portion of the heat withdrawn from the reaction product stream in the primary heat exchanger can be used for heating one or both of a pressurized steam stream and a pressurized $CO_2$ stream for use in power generation in a closed loop or semi-open loop power production system wherein a working stream is repeatedly compressed and expanded for power production.

A portion of the heat withdrawn from the reaction product stream in the primary heat exchanger can be used for heating a steam stream that is injected into the reactor.

Further processing the upgraded ethylene stream can comprise one or more of the following steps: passing the upgraded ethylene stream through an adsorber to adsorb any water in the upgraded ethylene stream; passing the upgraded ethylene stream through a refrigeration unit to cool the upgraded ethylene stream to a temperature of less than −50° C.; passing the upgraded ethylene stream through a de-methanizer unit; passing the upgraded ethylene stream through a de-ethanizer unit; passing a mixture of ethane and ethylene from the de-ethanizer into a C2 splitter unit.

The method can comprise injecting steam into the reactor.

In one or more embodiments, the present disclosure can related to systems for chemical production from ethane. In example embodiments, such systems can comprise: a catalytic reactor configured for reacting ethane with carbon dioxide at a temperature of about 450° C. or greater to form a reaction product stream including at least ethylene and carbon dioxide; an ethane line configured for delivery of ethane into the catalytic reactor; a carbon dioxide line configured for delivery of carbon dioxide into the catalytic reactor; a primary heat exchanger configured to receive the reaction product stream from the catalytic reactor and withdraw heat therefrom; a gas-liquid separation unit configured for removal of water and optionally other condensates from the reaction product stream; a compressor configured for compressing the reaction product to a pressure of at least 20 bar; a carbon dioxide separation unit configured for receiving the reaction product stream downstream of the primary heat exchanger and for separating at least a portion of the carbon dioxide from the reaction product stream to provide an upgraded ethylene stream; a line configured for delivering at least a portion of the carbon dioxide separated from the reaction product stream in the carbon dioxide separation unit to the reactor while being heated with at least a portion of the heat withdrawn from the reaction product stream in the primary heat exchanger. In further embodiments, the systems can be characterized by one or more of the following statements, which statements can be combined in any order or number.

The system can comprise a secondary heat exchanger, wherein the line configured for delivering at least a portion of the carbon dioxide separated from the reaction product stream in the carbon dioxide separation unit to the reactor can pass through the secondary heat exchanger for heating against a line passing a heated circulating stream from the primary heat exchanger.

The system can comprise a line heater configured for heating one or both of the ethane line and the carbon dioxide line.

The system can comprise one or more lines configured for delivering a heated stream from the primary heat exchanger to the line heater.

The system can comprise one or more lines configured for delivering a heated stream from the primary heat exchanger for transfer of heat to one or more of the following: the reactor; a carbon dioxide source; an ethane source.

The line configured for delivering at least a portion of the carbon dioxide separated from the reaction product stream in the carbon dioxide separation unit to the reactor can be specifically configured for delivering at least a portion of the carbon dioxide into one or both of the carbon dioxide line and the ethane line.

The system can comprise a thermal energy source configured for heating the reactor.

The thermal energy source can comprise one or more of the following: a concentrated solar energy heater; a combustion heater; a geothermal heater; an external industrial heat source.

The can comprise one or more of the following components configured for receiving the upgraded ethylene stream: a compressor configured for compressing the upgraded ethylene stream to a pressure of at least 10 bar; an adsorber configured for adsorbing any water in the upgraded ethylene stream; a refrigeration unit configured to cool the upgraded ethylene stream to a temperature of less than −50° C.; a de-methanizer unit; a de-ethanizer unit; a C2 splitter unit.

DETAILED DESCRIPTION

The present subject matter will now be described more fully hereinafter with reference to exemplary embodiments thereof. These exemplary embodiments are described so that this disclosure will be thorough and complete, and will fully convey the scope of the subject matter to those skilled in the art. Indeed, the subject matter can be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural referents unless the context clearly dictates otherwise.

The present disclosure relates to methods for chemical production from ethane. The disclosed methods utilize oxidative dehydrogenation of the ethane by carbon dioxide cracking. The reaction is preferably catalytic, and various catalysts may be used. For example, in some embodiments, a solid particle heater may be utilized as the reactor wherein particles coated with a mixed transition metal catalyst (or like material) can be heated (e.g., using concentrated solar power) to provide a hybrid thermal catalyst. Such hybrid thermal catalyst can be useful to drive a reaction for oxidative dehydrogenation of ethane to ethylene using carbon dioxide as a soft oxidant as shown below.

$$C_2H_6+CO_2+heat \rightarrow C_2H_4+H_2O+CO$$

The produced CO may be separated and fully oxidized to drive a turbine. Alternatively, a water gas shift reaction (WGSR) may be used with the produced $H_2O$ and CO to produce $H_2$ gas. This would provide a net reaction as shown below.

$$C_2H_6+heat \rightarrow C_2H_4+H_2$$

In such methods utilizing particle flow systems, the catalyst particles may be subjected to regeneration/cleaning, which can reduce interruptions in the process. Moreover, the process may be applied to a variety of industrial reactions by utilizing varying catalytic coatings on the particles. The catalyst may be provided as a coating on a variety of elements. For example, in some embodiments, the catalyst may be coated onto the inner surface of one or more pipes or tubes such that the catalytic reactions may occur as the ethane and carbon dioxide flow through the pipes and make contact with the catalyst.

Figure 1:
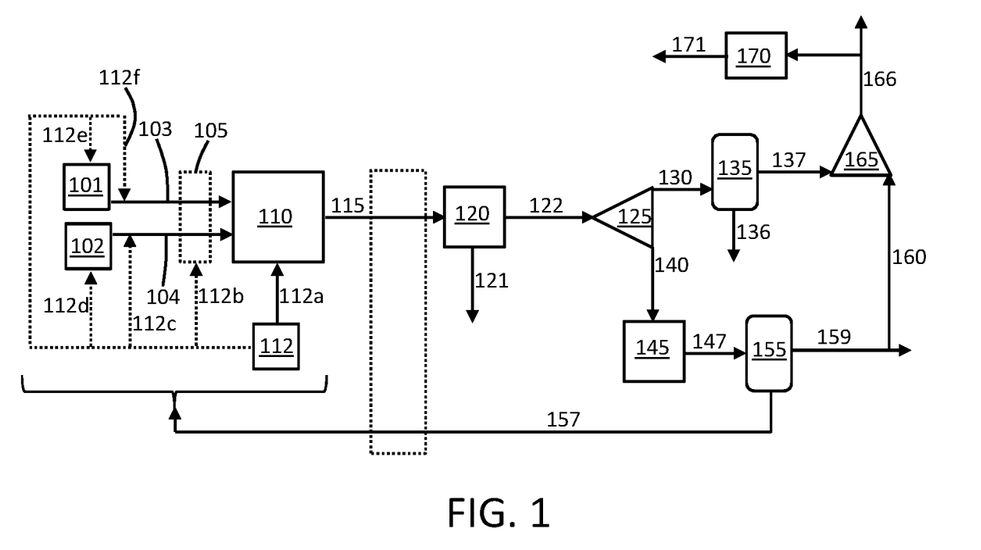
FIG. 1 is a flow diagram showing an example embodiment of a process wherein ethane is subjected to oxidative dehydrogenation utilizing carbon dioxide as a soft oxidant.

In one or more embodiments, a method for carbon dioxide cracking of ethane can be carried as generally described in the process diagram shown in FIG. 1. In particular, ethane from ethane source 101 is provided through line 103, and carbon dioxide from carbon dioxide source 102 is provided through line 104 into a reactor 110. The ethane and the carbon dioxide may be added separately to the reactor 110 or may be combined prior to passage into the reactor. In some embodiments, the ethane and/or the carbon dioxide in line 103 and line 104, respectively, may be passed through an optional line heater 105, which particularly may be configured for transfer of heat to one or more streams being passed to the reactor. The reactor 110 can be any suitable type of reactor, such as a fixed bed reactor catalytic reactor or a fluidized bed catalytic reactor containing a suitable catalyst. Additional catalyst may be added to the reactor 110 as needed. Thermal energy is supplied for the reaction from one or a combination of sources. As further described herein, recuperative heating may particularly be utilized. In addition, a thermal energy source 112 may supply the thermal energy to any one or a combination of the following: directly to the reactor 110 through line 112a; to the line heater 105 through line 112b; to the carbon dioxide line 104 through line 112c; to the carbon dioxide source 102 through line 112d; to the ethane source 101 through line 112e; to the ethane line 103 through line 112f. The thermal energy source 112 can be one, or a combination of the following sources of a thermal energy source; a concentrated solar energy heat source; a source for heat of combustion; an external industrial heat source.

Within the reactor 110, oxidative dehydrogenation (ODH) of ethane is performed to yield at least ethylene (and/or other suitable olefins), carbon monoxide, hydrogen, and water. As further described below, further chemical products likewise can be present in the reaction product stream and can be handled according to the present embodiment by combination of further steps as otherwise described herein. Returning to FIG. 1, the reaction product stream exits the reactor 110 in line 115 and is passed to an ethylene separation unit 120 from which ethylene is withdrawn in line 121. The remaining reaction product, including carbon monoxide, hydrogen, and water, exits in line 122.

The carbon monoxide, hydrogen, and water mixture in line 122 can be separated into two streams from separator 125. A mole (X) of the carbon monoxide, hydrogen, and water mixture is bled off in line 130 and cooled in condenser 135 to separate out water in line 136 via condensation and provide purified $CO/H_2$ in line 137. A mole fraction (1-X) of the carbon monoxide, hydrogen, and water mixture is bled off in line 140 and undergoes a water gas shift reaction in a WGS reactor 145 to provide a mixture of carbon dioxide and hydrogen gas in line 147. The mixture of carbon dioxide and hydrogen is separated in separator 155 to provide a stream of recycled carbon dioxide in line 157, which can be recycled into one or more of the following: directly into the reactor 110; into the carbon dioxide source 102; into the carbon dioxide line 104; into the line heater 105; into the ethane source 101; into the ethane line 103. The carbon dioxide in the line 157 may be heated utilizing waste heat taken from the reaction product in line 115, such as using an optional recuperator heat exchanger 162. The separator 155 utilized to separate hydrogen gas from the carbon dioxide can utilize any one or more of the following separation methods: pressure swing adsorption (PSA); membrane separation; cryogenic separation. The resulting hydrogen stream leaving in line 159 can be compressed (e.g., to a pressure of at least 20 bar, at least 30 bar, or at least 50 bar, such as from about 20 bar to about 150 bar, about 30 bar to about 125 bar, or about 50 bar to about 100 bar, specifically to about 74 bar) for providing as a commodity or for use in power production. In some embodiments, at least a portion of the hydrogen in line 159 may be passed through line 160 to union 165 to be combined with at least a portion of the carbon monoxide from line 137 to provide a stream of combined carbon monoxide and hydrogen gas in line 166. The stream of combined carbon monoxide and hydrogen gas in line 166 can be exported as a synthesis gas product to be used in power production. Likewise, at least a portion of the synthesis gas exported from line 166 may be combusted for heat production in thermal energy source 112. If desired, at least a portion of combined carbon monoxide and hydrogen gas in line 166 can be provided through line 167 into synthesis unit 170 for production of further chemicals. For example, the synthesis unit 170 may comprise a methanol synthesis unit, and the mixture of combined carbon monoxide and hydrogen gas can be utilized for methanol synthesis. In such instances, the produced methanol in line 171 can be subjected to a dehydration reaction producing a separate stream of ethylene and water.

Figure 2:
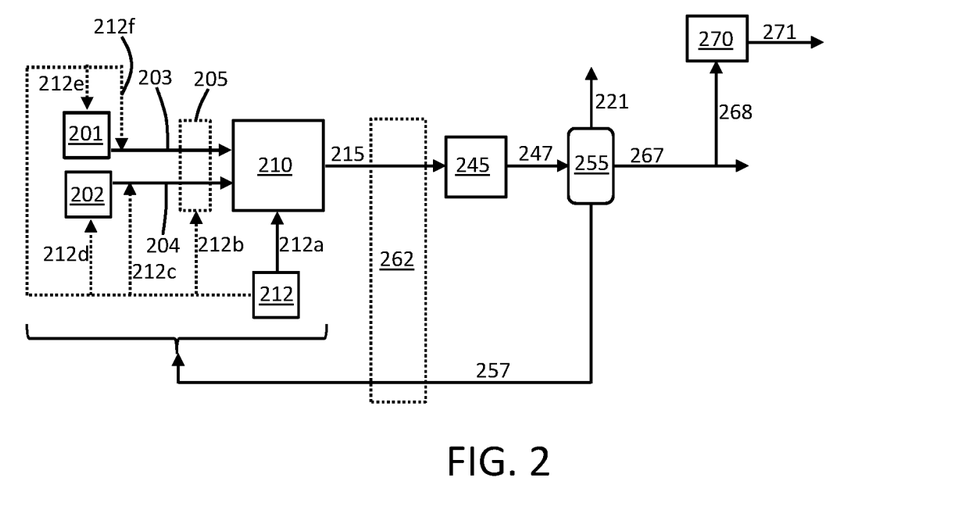
FIG. 2 is a flow diagram showing another example embodiment of a process wherein ethane is subjected to oxidative dehydrogenation utilizing carbon dioxide as a soft oxidant.

A further example embodiment of the present method is illustrated in FIG. 2. As seen therein, ethane from ethane source 201 is provided through line 203, and carbon dioxide from carbon dioxide source 202 is provided through line 204 into a reactor 210. The ethane and the carbon dioxide may be added separately to the reactor 210 or may be combined prior to passage into the reactor. In some embodiments, the ethane and/or the carbon dioxide in line 203 and line 204, respectively, may be passed through an optional line heater 205, which particularly may be configured for transfer of heat to one or more streams being passed to the reactor. The reactor 210 again can be any suitable type of reactor; however, it preferably is a catalytic reactor containing a suitable catalyst (which may be replenished as needed through addition of make-up catalyst). Thermal energy is supplied for the reaction from one or a combination of sources, as already described. Specifically, a thermal energy source 212 may supply the thermal energy to any one or a combination of the following: directly to the reactor 210 through line 212a; to the line heater 205 through line 212b; to the carbon dioxide line 204 through line 212c; to the carbon dioxide source 202 through line 212d; to the ethane source 201 through line 212e; to the ethane line 203 through line 212f.

Within the reactor 210, oxidative dehydrogenation (ODH) of ethane is performed to yield at least ethylene (and/or other suitable olefins), carbon monoxide, hydrogen, and water. The reaction product stream exits the reactor 210 in line 215 and is passed to WGS reactor 245 to provide a mixed stream of carbon monoxide, hydrogen, carbon dioxide, and ethylene in line 247. The molar fraction of carbon monoxide and hydrogen provided in line 247 can be tuned to various ratios dependent upon the extent of the reaction in the WGS reactor 245. The mixed stream of carbon monoxide, hydrogen, carbon dioxide, and ethylene is passed through separator 255 to be separated into three streams. A first stream formed of recycled carbon dioxide passes through stream 257 to be recycled into one or more of the following: directly into the reactor 210; into the carbon dioxide source 202; into the carbon dioxide line 204; into the line heater 205; into the ethane source 201; into the ethane line 203. The carbon dioxide in the line 257 may be heated utilizing waste heat taken from the reaction product in line 215, such as using an optional recuperator heat exchanger 262. A second stream formed of ethylene leaves in line 221. A third stream comprising a mixture of carbon monoxide, hydrogen, and carbon dioxide leaves in line 267 and can be processed for further chemical production. For example, at least a portion of the mixture of carbon monoxide, hydrogen, and carbon dioxide can be passed through line 268 into a methanol synthesis unit 270 to produce methanol in line 271, which can be subjected to a dehydration reaction producing a separate stream of ethylene and water.

In one or more embodiments, the presently disclosed methods can be particularly useful in that the amount of carbon dioxide utilized in the cracking process can be beneficially increased beyond the required amount so that the reaction stream can include an excess of carbon dioxide. This can include providing ethane and carbon dioxide into the reactor at a molar ratio so that the amount of provided carbon dioxide is in excess of the stoichiometrically required amount for complete reaction with the ethane. The molar excess of carbon dioxide can be sufficient so that the reaction product exiting the reactor can comprise at least 5% by mass, at least 10% by mass, at least 20% by mass, at least 25% by mass, at least 30% by mass, or at least 40% by mass carbon dioxide, particularly up to a maximum of about 80% by mass carbon dioxide, based on the total mass of the reaction product exiting the reactor. In preferred embodiments, the reaction product exiting the reactor can comprise about 5% to about 70%, about 10% to about 60%, or about 20% to about 50% by mass carbon dioxide, based on the total mass of the reaction product exiting the reactor. The presence of excess carbon dioxide is beneficial for multiple reasons. For example, the provision of excess carbon dioxide can ensure that maximum ethane conversion occurs in the reactor. It further can provide a large mass of recyclable material that can reduce the amount of make-up carbon dioxide that may be replenished into the reactor. It still further can provide a large amount of heat that can be recuperated to reduce the amount of energy that must be expended for heating in the reactor.

Figure 3:
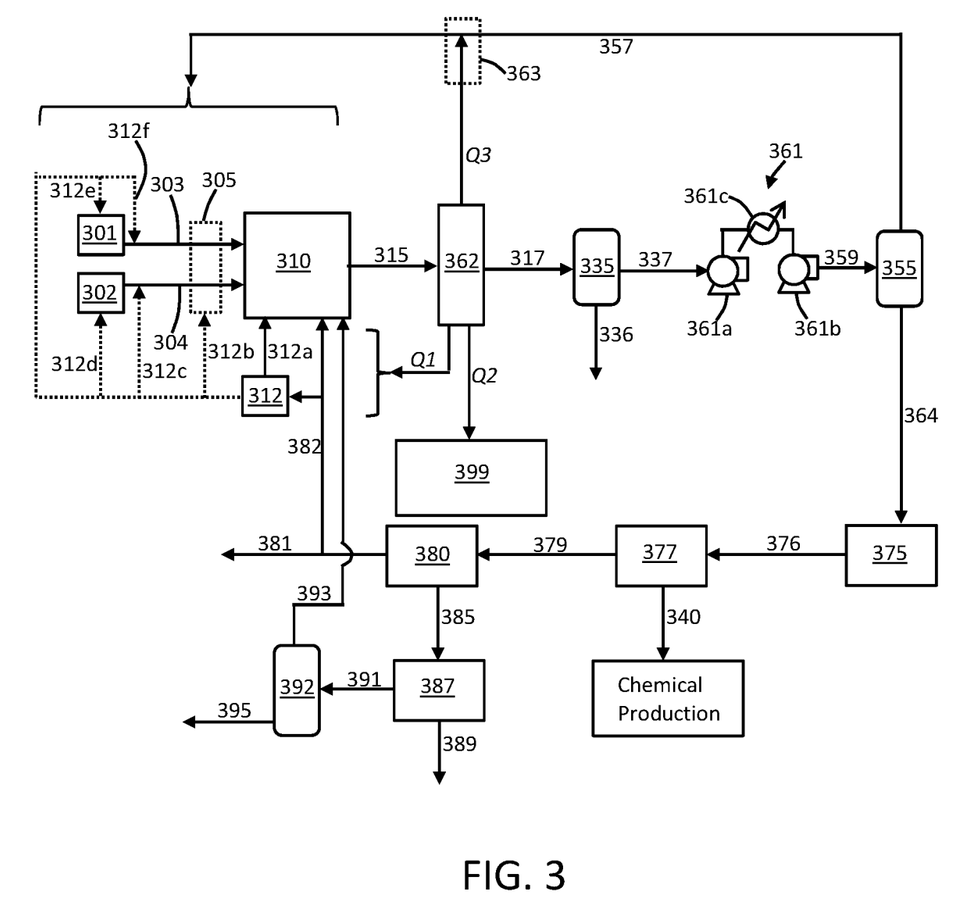
FIG. 3 is a flow diagram showing yet another example embodiment of a process wherein ethane is subjected to oxidative dehydrogenation utilizing carbon dioxide as a soft oxidant.

The advantages of utilizing an excess of carbon dioxide in the reaction is further illustrated in relation to FIG. 3. As seen therein, ethane from ethane source 301 is provided through line 303, and carbon dioxide from carbon dioxide source 302 is provided through line 304 into a reactor 310. The ethane and the carbon dioxide may be added separately to the reactor 310 or may be combined prior to passage into the reactor. In some embodiments, the ethane and/or the carbon dioxide in line 303 and line 304, respectively, may be passed through an optional line heater 305, which particularly may be configured for transfer of heat to one or more streams being passed to the reactor. The reactor 310 again can be any suitable type of reactor; however, it preferably is a catalytic reactor containing a suitable catalyst (which may be replenished as needed through addition of make-up catalyst). Thermal energy is supplied for the reaction from one or a combination of sources, as already described. Specifically, a thermal energy source 312 may supply the thermal energy to any one or a combination of the following: directly to the reactor 310 through line 312a; to the line heater 305 through line 312b; to the carbon dioxide line 304 through line 312c; to the carbon dioxide source 302 through line 312d; to the ethane source 301 through line 312e; to the ethane line 303 through line 312f. In a particular embodiment, both of the ethane in line 303 and the carbon dioxide in line 304 are preheated in the line heater 305 prior to being sent to the reactor 310. Such heating alone can be sufficient to provide the desired reaction temperature within the reactor 301; however, further heating can be provided directly to the reactor. In some embodiments, a steam stream may be provided in line 312a to deliver thermal energy from the thermal energy source 312. Alternatively, a steam stream may be provided in addition to the thermal energy from the thermal energy source.

The reaction within the reactor is preferably carried out at a temperature of at least 450° C., at least 475° C., or at least 500° C., such as up to a maximum temperature of about 1000° C. In preferred embodiments, the temperature within the reactor 310 for reaction to occur is in the range of about 450° C. to about 1000° C., about 500° C. to about 800° C., or about 550° C. to about 700° C. Such temperatures can further apply to other embodiments described herein. The reaction of ethane with carbon dioxide in the reactor produces a reaction product stream comprising at least ethylene, carbon monoxide, water, and carbon dioxide, but also can include unreacted ethane, hydrogen, methane, and traces of heavier hydrocarbons. The mixture of reaction produces exits the reactor 310 in line 315 and is passed into a heat exchanger 362. The heat exchanger 362 can be referenced as a primary heat exchanger 362 for simplicity of identification. In an example embodiment, the heat exchanger 362 can be a transfer line exchanger (TLE). Passage through the TLE rapidly cools the reaction product down to a temperature of about 200° C. to about 400° C., which is beneficial to substantially prevent further occurrence of side reactions and thus reduce or eliminate production of undesired by-products. Waste heat (Q) withdrawn from the reaction product stream can be utilized for multiple purposes. For example, the waste heat may be utilized to preheat the reactor feed streams. As such, heat provided through one or more of streams 312a through 312f may be heat provided from heat exchanger 362. In this manner, heat withdrawn from the reaction product stream may be used to heat the ethane stream and/or the carbon dioxide stream. Likewise, heat withdrawn from the reaction product stream may be used to provide heat directly to the reactor 310. As illustrated in FIG. 3, a first heat quantity (Q1) is withdrawn from the heat exchanger 362 to be used to provide heat to any of the reactor 310, the ethane source 301, the ethane line 303, the carbon dioxide source 302, and the carbon dioxide line 304. In further embodiments, as illustrated in FIG. 3, waste heat (Q2) from the heat exchanger 362 can be used to heat a high pressure steam stream and/or a high pressure $CO_2$ stream for use in power generation in a closed loop or semi-open loop power production system wherein a working stream is repeatedly compressed and expanded for power production. As such, the presently disclosed methods can be reliably combined with any systems and methods that are known for power production, and particularly with systems and methods that are known to produce $CO_2$. For example, U.S. Pat. Nos. 8,596,075, 8,776,532, 8,959,887, 8,986,002, 9,068, 743, 9,416,728, 9,546,814, 10,018,115, and U.S. Pub. No. 2012/0067054, the disclosures of which are incorporated herein by reference, all describe system and methods that may be combined with the presently disclosed methods. Such systems and methods can be a reliable source of $CO_2$ for use in the chemical conversion process. Likewise, waste heat from heat exchanger 362 may be used to provide added heating in such systems and methods.

The reaction product stream, after being cooled in the heat exchanger 362, can be passed through line 317 to a gas-liquid separator 335, such as a water separation tower or other condensing unit in order to further cool the reaction product stream to approximately ambient temperature and remove water and other condensates by use of a quench water or quench oil. As shown in FIG. 3, water and any entrained condensates are withdrawn through stream 336.

The reaction product stream can be subject to a variety of process steps by passage through one or more system units in order to upgrade the ethylene concentration in the reaction product stream. An upgraded ethylene stream thus can be defined as a stream comprising a higher weight percentage of ethylene than the stream from which it was derived. This can be achieved through, for example, removal of one or more other components from the reaction product stream, such as carbon dioxide, hydrogen sulfide, and other acid gases. In some embodiments, an enriched or upgraded ethylene stream may be referred to as a cleaned reaction product stream since it still contains at least a portion of the reaction products (e.g., ethylene) and has been cleaned of at least a portion of the non-ethylene constituents (e.g., carbon dioxide, water, etc.).

The reaction product stream is preferably compressed to enhance the separation of further components of the reaction product stream, such as through use of absorbents, adsorbents, and/or membrane separators. The high pressure operation of downstream units, such as the carbon dioxide separator 355, can also be useful to reduce the equipment size and thus the required capital cost.

The quenched reaction product stream in line 337 can be compressed to a pressure of at least 20 bar, at least 25 bar, or at least 30 bar (e.g., with a maximum of about 100 bar), and preferably is compressed to a pressure of about 10 bar to about 100 bar, about 20 bar to about 90 bar, or about 30 bar to about 80 bar. As illustrated, in FIG. 3, the compression is carried out using a multi-stage intercooled centrifugal compressor 361; however, any alternative compressor suitable to provide the necessary compression may be used. Optionally, a caustic soda wash can be applied at the exit of each compression stage to remove traces of acid gas from the process stream.

The quenched and compressed reaction product stream in line 359 can be directed to a carbon dioxide separator 355 wherein carbon dioxide is separated from the reaction product stream to form a first ethylene-enriched stream in line 364 and a recycled carbon dioxide stream in line 357. The first ethylene-enriched stream in line 364 can be considered to be an upgraded ethylene stream because the weight percentage of ethylene in the stream in line 364 is greater than the weight percentage of ethylene in the quenched reaction product stream in line 337 and/or the compressed reaction product stream in line 359. The recycled carbon dioxide in stream 357 can be heated using waste heat (Q3) from the heat exchanger 362. It is understood that in any or all cases wherein waste heat is utilized, the stream being heated may pass through the heat exchanger 362, or a secondary circulating heating fluid may be circulated through the heat exchanger for heat transfer to the further stream being heated. As such, one or more additional heat exchangers may be utilized to transfer heat from a circulating fluid to the stream in a given line without commingling of the streams. As illustrated in FIG. 3, the recycled carbon dioxide in stream 357 can be heated with waste heat (Q3) by passage through the secondary heat exchanger 363. In an example embodiment, a circulating fluid may be circulated through the primary heat exchanger 362 and the secondary heat exchanger 363 so that the carbon dioxide in line 357 is heated using the heat withdrawn from the reaction product stream in the primary heat exchanger 362. Although not shown in FIG. 3, is understood that the line (Q3) would pass from the secondary heat exchanger 363 and back into the primary heat exchanger 362 for further withdrawal of heat from the reaction product stream. The recycled carbon dioxide in stream 357 that is heated with waste heat (Q3) may be combined with any one or more of the following to provide heating: the reactor 310; the carbon dioxide source 302; the carbon dioxide line 304; the line heater 305; the ethane source 301; the ethane line 303. In this manner, the recycled carbon dioxide can be recycled back for the dehydrogenation reaction with fresh ethane and reduce the amount of added carbon dioxide that must be added to the reaction.

The carbon dioxide separator 355 can be configured to utilize a variety of unit operations such as an absorption tower, an adsorption bed, a membrane-based separator, a refrigeration process, or any combination thereof. Separation of the carbon dioxide is preferred to be carried prior to downstream separation of hydrocarbon and other species within the reaction product stream as such separation typically involves refrigeration and cooling of process gas to temperatures that exceeds the triple point of carbon dioxide, and cooling the carbon dioxide to such temperature can cause sublimation and formation of solid carbon dioxide within the piping and equipment.

Although the carbon dioxide separator 355 is illustrated as being downstream from the compressor 361, in some embodiments, carbon dioxide separation may be carried out between compression states. As such, the reaction product stream in line 337 may first pass to a first stage compressor 361a, then to a carbon dioxide separator 355, and then to a second stage compressor 361b. The carbon dioxide separator 355, for example, may be positioned between an intercooler 361c and the second stage compressor 361b. In further embodiments, the carbon dioxide separator 355 may be configured to be fully upstream from the compressor 361. As such, substantially no compression may be carried out prior to carbon dioxide separation. In further embodiments, however, a supplemental compressor may be provided downstream from the gas-liquid separator 335 to compress the reaction product stream to a first pressure (e.g., up to about 15 bar, such as about 5 bar to about 15 bar) at which carbon dioxide separation is carried out, and the reaction product stream exiting the carbon dioxide separator may be passed to the compressor 361 to be compressed to a second, greater pressure.

The compressed, first ethylene-enriched stream exits the carbon dioxide separator 355 in line 364 and is passed to an adsorber 375, which can comprise an adsorbent bed of appropriate material (such as molecular sieves). The material utilized in the adsorber 375 is preferably configured to remove traces of moisture which could otherwise freeze and form ice in the downstream piping and equipment that are operated below the freezing point of water.

The dried and pressurized first ethylene-enriched stream exiting the adsorber in line 376 is then fed into a refrigeration unit 377 where it is cooled to a temperature that is less than −50° C., less than −100° C., or less than −150° C., preferably being cooled to a temperature range of about −50° C. to about −200° C., about −100° C. to about −190° C., or about −150° C. to about −180° C., particularly to a temperature of about −165° C. The dried and pressurized first ethylene-enriched stream is preferably at a temperature and pressure such that hydrogen and carbon monoxide present in the stream remains in the vapor stage while other constituents of first ethylene-enriched stream will liquefy and can be separated therefrom. As such, the refrigeration unit 377 can comprise a phase separator.

Exiting the refrigeration unit in stream 340 is a mixture of carbon monoxide and hydrogen which can be used in chemical production as already described above. For example, the mixture of carbon monoxide and hydrogen in stream 340 can be passed to a WGS reactor 345 to provide a mixed stream of carbon monoxide and hydrogen, which can be used in downstream chemical production, such as methanol and/or Fischer-Tropsch (FT) synthesis. The ratio of carbon monoxide and hydrogen can be optionally adjusted in a water-gas shift step to meet the chemical production requirement.

A second ethylene-enriched stream exits the refrigeration unit 377 in line 379 and is fed to a de-methanizer unit 380 to separate any methane therefrom. Further to the above discussion, the second ethylene-enriched stream in line 379 can be considered to be an upgraded ethylene stream since it comprises a greater weight percentage of ethylene when compared to the stream immediately upstream in line 376 that is passed through the refrigeration unit 377. A methane-rich stream exits the de-methanizer unit 380 in line 381. The methane-rich stream may be exported as a commodity. In some embodiments, at least a portion of the methane may be withdrawn in line 382 to be utilized in the reactor 310 to provide reaction heating and/or to be utilized in thermal energy source 312 to provide combustion heating.

A third ethylene-enriched stream (which likewise can be considered to be an upgraded ethylene stream) also exits the de-methanizer unit 380 in line 385 and is fed to a de-ethanizer column 387. A bottom product comprised of C3 and greater hydrocarbons is bled off in line 389. In some embodiments, methane and other light gases from the top section of the de-methanizer column unit can be used as a supplementary fuel for sue in the reactor 310 and/or the thermal energy source 312. In further embodiments, uncoverted ethane from the C2 splitter can be used as a supplementary fuel for sue in the reactor 310 and/or the thermal energy source 312.

A fourth-ethylene enriched stream (comprising predominately ethylene and ethane) is passed through line 391 into a C2-splitter column 392 to further fractionate the stream into its main constituents, ethylene and ethane. An overhead ethane stream in line 393 from the C2-splitter column 392 is recycled back to the dehydrogenation reactor 310. A stream of purified ethylene leaves the bottom of the C2-splitter column 392 in line 395. The separation and purification of heavier hydrocarbons in the stream from the bottom of the de-ethanizer unit 387 can be carried out in any appropriate combinations of de-propanizer/C3-splitter, debutanizer/C4-splitter and so on.

As seen from the foregoing, the present disclosure provides a sustainable and environmentally friendly method for the production of ethylene, $H_2$, and methanol, which are the three most fundamental building blocks for the chemical industry globally. Ethylene is the most produced organic compound on earth, and it is known to be used in numerous products. The presently disclosed methods can enable industry to produce ethylene using less energy, while producing $H_2$, methanol, and even further chemical products as well. Moreover, the disclosed methods also consume $CO_2$ by essentially "fixing" it into compounds whose ultimate use will not re-emit that $CO_2$.

Many modifications and other embodiments of the presently disclosed subject matter will come to mind to one skilled in the art to which this subject matter pertains having the benefit of the teachings presented in the foregoing descriptions and the associated drawings. Therefore, it is to be understood that the present disclosure is not to be limited to the specific embodiments described herein and that modifications and other embodiments are intended to be included within the scope of the appended claims. Although specific terms are employed herein, they are used in a generic and descriptive sense only and not for purposes of limitation

The invention claimed is:

1. A method for chemical production from ethane, the method comprising:
    providing ethane and carbon dioxide into a reactor at a molar ratio so that the amount of provided carbon dioxide is in excess of the stoichiometrically required amount for complete reaction with the ethane;
    reacting the ethane with the carbon dioxide in the reactor in the presence of a catalyst to form a reaction product stream comprising at least ethylene, water, and carbon dioxide, the reaction product stream being at a temperature of about 450° C. or greater;
    passing the reaction product stream through a primary heat exchanger to withdraw heat therefrom;
    removing water and optionally any further condensates present in the reaction product stream;
    compressing the reaction product stream to a pressure of at least 20 bar;
    separating carbon dioxide from the reaction product stream in a separation unit to provide an upgraded stream comprising ethylene;
    heating at least a portion of the carbon dioxide separated from the reaction product stream using the heat withdrawn from the reaction product stream to form a stream of heated carbon dioxide;
    recycling the stream of heated carbon dioxide back into the reactor; and
    further processing the upgraded stream comprising ethylene to provide at least ethylene as a produced chemical.

2. The method of claim 1, wherein the reactor is a fixed bed reactor, a catalytic reactor, or a fluidized bed catalytic reactor.

3. The method of claim 1, wherein the reaction product stream is at a temperature of about 500° C. to about 800° C.

4. The method of claim 1, wherein the reaction product stream comprises at least 10% by mass carbon dioxide based on the total mass of the reaction product exiting the reactor.

5. The method of claim 1, wherein the reaction product stream comprises about 10% to about 60% by mass carbon dioxide, based on the total mass of the reaction product exiting the reactor.

6. The method of claim 1, wherein the primary heat exchanger is a transfer line exchanger (TLE).

7. The method of claim 1, wherein the reaction product stream exiting the primary heat exchanger is at a temperature of about 200° C. to about 400° C.

8. The method of claim 1, wherein removing water and optionally any further condensates present in the reaction product comprises passing the reaction product stream through a condensing unit.

9. The method of claim 8, wherein the reaction product stream is cooled in the condensing unit to about ambient temperature.

10. The method of claim 1, wherein heating at least a portion of the carbon dioxide separated from the reaction product stream using the heat withdrawn from the reaction product stream comprises passing the carbon dioxide through a secondary heat exchanger against a circulating stream that is heated in the primary heat exchanger using the heat withdrawn from the reaction product stream.

11. The method of claim 1, wherein recycling the stream of heated carbon dioxide back into the reactor comprises one or more of the following:
injecting the stream of heated carbon dioxide directly into the reactor;
injecting the stream of heated carbon dioxide into a carbon dioxide source;
injecting the stream of heated carbon dioxide into a line delivering carbon dioxide from a carbon dioxide source to the reactor;
injecting the stream of heated carbon dioxide into an ethane source;
injecting the stream of heated carbon dioxide into a line delivering ethane from an ethane source to the reactor.

12. The method of claim 1, wherein the at least a portion of the stream of heated carbon dioxide is passed through a line heater configured for transfer of heat from the stream of heated carbon dioxide to one or more streams being passed into the reactor.

13. The method of claim 1, wherein a portion of the heat withdrawn from the reaction product stream in the primary heat exchanger is used for heating one or more of the following:
the reactor;
a carbon dioxide source;
a carbon dioxide line delivering carbon dioxide from a carbon dioxide source to the reactor;
an ethane source;
an ethane line delivering ethane from an ethane source to the reactor.

14. The method of claim 1, wherein a portion of the heat withdrawn from the reaction product stream in the primary heat exchanger is used for heating one or both of a pressurized steam stream and a pressurized $CO_2$ stream for use in power generation in a closed loop or semi-open loop power production system wherein a working stream is repeatedly compressed and expanded for power production.

15. The method of claim 1, wherein a portion of the heat withdrawn from the reaction product stream in the primary heat exchanger is used for heating a steam stream that is injected into the reactor.

16. The method of claim 1, wherein further processing the upgraded ethylene stream comprises one or more of the following steps:
passing the upgraded ethylene stream through an adsorber to adsorb any water in the upgraded ethylene stream;
passing the upgraded ethylene stream through a refrigeration unit to cool the upgraded ethylene stream to a temperature of less than −50° C.;
passing the upgraded ethylene stream through a de-methanizer unit;
passing the upgraded ethylene stream through a de-ethanizer unit to produce a mixture of ethane and ethylene, and passing the mixture of ethane and ethylene from the de-ethanizer unit into a $C_2$ splitter unit.

17. The method of claim 1, comprising injecting steam into the reactor.

18. A system for chemical production from ethane, the system comprising:
a catalytic reactor configured for reacting ethane with carbon dioxide at a temperature of about 450° C. or greater to form a reaction product stream including at least ethylene and carbon dioxide;
an ethane line configured for delivery of ethane into the catalytic reactor;
a carbon dioxide line configured for delivery of carbon dioxide into the catalytic reactor;
a primary heat exchanger configured to receive the reaction product stream from the catalytic reactor and withdraw heat therefrom;
a gas-liquid separation unit configured for removal of water and optionally other condensates from the reaction product stream;
a compressor configured for compressing the reaction product stream to a pressure of at least 20 bars;
a carbon dioxide separation unit configured for receiving the reaction product stream after at least one stage of compression and for separating at least a portion of the carbon dioxide from the reaction product stream to provide an upgraded stream comprising ethylene; and
a line configured for delivering at least a portion of the carbon dioxide separated from the reaction product stream in the carbon dioxide separation unit to the reactor while being heated with at least a portion of the heat withdrawn from the reaction product stream in the primary heat exchanger.

19. The system of claim 18, comprising a secondary heat exchanger, wherein the line configured for delivering at least a portion of the carbon dioxide separated from the reaction product stream in the carbon dioxide separation unit to the reactor passes through the secondary heat exchanger for heating against a line passing a heated circulating stream from the primary heat exchanger.

20. The system of claim 18, comprising a line heater configured for heating one or both of the ethane line and the carbon dioxide line.

21. The system of claim 20, comprising one or more lines configured for delivering a heated stream from the primary heat exchanger to the line heater.

22. The system of claim 18, comprising one or more lines configured for delivering a heated stream from the primary heat exchanger for transfer of heat to one or more of the following:
the reactor;
a carbon dioxide source;
an ethane source.

23. The system of claim 18, wherein the line configured for delivering at least a portion of the carbon dioxide separated from the reaction product stream in the carbon dioxide separation unit to the reactor is specifically configured for delivering at least a portion of the carbon dioxide into one or both of the carbon dioxide line and the ethane line.

24. The system of claim 18, comprising a thermal energy source configured for heating the reactor.

25. The system of claim 24, wherein the thermal energy source comprises one or more of the following: a concentrated solar energy heater; a combustion heater; an external industrial heat source.

26. The system of claim 18, comprising one or more of the following components configured for receiving the upgraded stream comprising ethylene:
- a compressor configured for compressing the upgraded ethylene stream to a pressure of at least 10 bar;
- an adsorber configured for adsorbing any water in the upgraded ethylene stream;
- a refrigeration unit configured to cool the upgraded ethylene stream to a temperature of less than −50° C.;
- a de-methanizer unit;
- a de-ethanizer unit;
- a C2 splitter unit.

\* \* \* \* \*